US00PP24389P3

(12) United States Plant Patent
Suphachadiwong

(10) Patent No.: US PP24,389 P3
(45) Date of Patent: Apr. 15, 2014

(54) ***PHALAENOPSIS* PLANT NAMED 'SUPHAL1201'**

(50) Latin Name: ***Phalaenopsis* hybrid**
Varietal Denomination: SUPHAL1201

(75) Inventor: Thumrong Suphachadiwong, Chonburi (TH)

(73) Assignee: Suphachatwong Innovation Co., Ltd (TH)

( * ) Notice: Subject to any disclaimer, the term of this patent is extended or adjusted under 35 U.S.C. 154(b) by 0 days.

(21) Appl. No.: 13/573,446

(22) Filed: Sep. 14, 2012

(65) Prior Publication Data

US 2014/0082785 P1 Mar. 20, 2014

(51) Int. Cl.
*A01H 5/00* (2006.01)

(52) U.S. Cl.
USPC ..... Plt./311

(58) Field of Classification Search
USPC ..... Plt./311
See application file for complete search history.

*Primary Examiner* — Kent L Bell
(74) *Attorney, Agent, or Firm* — Cassandra Bright

(57) ABSTRACT

A new and distinct *Phalaenopsis* cultivar named 'SUPHAL1201' is disclosed, characterized by exceptionally high flower count per plant and obovate shaped flowers. Plants are unusually compact. The new variety is a *Phalaenopsis*, typically produced as an indoor ornamental plant.

1 Drawing Sheet

Latin name of the genus and species: *Phalaenopsis* hybrid. Variety denomination: 'SUPHAL1201'.

BACKGROUND OF THE INVENTION

This application relates to a new cultivar of *Phalaenopsis* hybrid. The new variety is the product of a planned breeding program. The new variety originated as a seedling from the crossing of the unpatented, proprietary seed parent *Phalaenopsis* 'S4WL1' with the unpatented, proprietary pollen parent referred to as *Phalaenopsis* 'S5BTX'. The crossing was made by the inventor in his research greenhouse in Chonburi, Thailand in May of 2005.

The new variety was first selected by the inventor, Thumrong Suphachadiwong, a citizen of Thailand, in March of 2008, in a research greenhouse belonging to the inventor in Chonburi, Thailand. After identifying the new variety as a potentially interesting selection, the inventor continued confidential testing and propagation of 'SUPHAL1201', assessing stability of the unique characteristics of this variety.

Asexual reproduction of the new cultivar 'SUPHAL1201' was first performed at a commercial laboratory in Chonburi, Thailand by tissue culture in March of 2008. Access to all plants was restricted, as plants were kept in a greenhouse not open to the public, and tissue culture plantlets were in a laboratory belonging to the inventor, and not accessible to the public. Through subsequent propagation, multiple generations have been reproduced, which have shown that the unique features of this cultivar are stable and reproduced true to type.

SUMMARY OF THE INVENTION

The cultivar 'SUPHAL1201' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SUPHAL1201.' These characteristics in combination distinguish 'SUPHAL1201' as a new and distinct *Phalaenopsis* cultivar:

1. Significant high flower count per plant.
2. Unusual compact plant shape.
3. Obovate flower shape.

PARENT COMPARISON

Plants of the new cultivar 'SUPHAL1201' are similar to the seed parent, *Phalaenopsis* 'S4WL1' in most horticultural characteristics. The new variety, however, produces flowers larger in size and of different color than the seed parent.

Plants of the new cultivar 'SUPHAL1201' are similar to the pollen parent, *Phalaenopsis* 'S5BTX' in most horticultural characteristics. Plants of the new variety, however, produce flowers that are smaller in size than the pollen parent.

COMMERCIAL COMPARISON

'SUPHAL1201' is similar in most horticultural characteristics to the unpatented commercial variety *Phalaenopsis* 'Wedding Bells' in most horticultural characteristics. The new variety, however, produces shorter leaves than 'Wedding Bells', and different shaped petals. Additionally, the new variety has a yellow and white lip coloration, whereas 'Wedding Bells' has a yellow lip coloration.

'SUPHAL1201' is similar in most horticultural characteristics to the unpatented commercial variety *Phalaenopsis* 'Sao Paulo' in most horticultural characteristics. The new variety, however, produces lighter colored leaves than 'Sao Paulo'. The peduncles of 'San Paulo' have less anthocyanin coloration than those produced by the new variety. Further more the petal shape of the new variety is different than 'Sao Paulo'.

BRIEF DESCRIPTION OF THE PHOTOGRAPH

The accompanying photograph in FIG. 1 illustrates in full color a typical plant of 'SUPHAL1201' grown in a commercial greenhouse in Zuidbroek, the Netherlands. This plant is approximately 18 months old after deflasking, shown planted in an 11 cm container. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'SUPHAL1201' plants grown in a greenhouse in Zuidbroek, the Netherlands. Temperatures ranged between 18° C. and 28° C. day and night. No photoperiodic or chemical treatments were given to the plants. During bright Summer conditions, shade was given. During dark Winter months, supplemental light was given at unspecified amounts. Measurements and numerical values represent averages of typical plant types.

Botanical classification: *Phalaenopsis* hybrid 'SUPHAL1201'.

PROPAGATION

Type of propagation typically used: Tissue culture.

Time to initiate roots: About 21 days at approximately 28° C.

Time to produce a rooted cutting/liner: About 26 weeks at approximately 18° C. to 28° C.

Root description: Thick (typical for *Phalaenopsis*) and rounded, average diameter: 5 mm, colored greyed-green, near RHS 194A and 198D.

PLANT

Growth habit: Monopodial.

Height from to of soil line to top of foliage: Average 13.0 cm.

Height from to of soil line to top of flowers: Average 32.5 cm.

Plant spread: At widest, average: 20.5 cm; at narrowest: 30.0 cm.

Normal pot size: 11 cm.

Growth rate: Moderate.

Number of leaves per plant: Average 10.

FOLIAGE

Leaf:

*Arrangement*.—Distichous.

*Average length*.—Approximately 12.2 cm.

*Average width*.—Approximately 4.6 cm.

*Shape of blade*.—Narrow obovate.

*Aspect*.—Downwardly arching.

*Apex*.—Unequal acute.

*Base*.—Cuneate. Sheath length: Average 1.2 cm. Sheath width: Average.0.8 cm. Sheath color: Yellow-green, near RHS 144A and 146B.

*Margin*.—Entire.

*Texture of top surface*.—Smooth, glossy, slightly furrowed.

*Texture of bottom surface*.—Smooth, glossy, slightly furrowed.

*Color*.—Young foliage upper side: Green to yellow-green, near RHS 137B and 147B. Young foliage under side: Yellow-green, near RHS 144A and 146B. Mature foliage upper side: Green RHS 137B. Mature foliage under side: Yellow-green, near RHS 144A.

*Venation*.—Type: Camptodromous. Venation coloration: All lateral veins Yellow-green, near RHS 144A, main vein on under side green, near RHS 143A.

Petiole: No petioles present.

FLOWERING CHARACTERISTICS

Flower bud:

*Rate of opening*.—Approximately 5 days after bud stage described.

*Length*.—Approximately 1.5 cm.

*Diameter*.—Approximately 1.1 cm wide and 1.3 cm high.

*Shape*.—Broad ovate.

*Color*.—Yellow-green, near RHS 150D, upper side heavily tinged greyed-red, near RHS 182D, 182C and 182B.

Peduncle:

*Length*.—Approximately 30.8 cm.

*Width*.—Approximately 0.4 cm.

*Aspect*.—Approximately 70° angle to rosette.

*Strength*.—Strong.

*Texture*.—Smooth, not very glossy.

*Color*.—Yellow-green, near RHS 146A, heavily marbled greyed-purple to Brown, in between near RHS 186C and 200A.

Inflorescence:

*Flowers per stem*.—Average 11.

*Inflorescence per plant*.—Average 3.

*Inflorescence arrangement*.—Raceme.

*Inflorescence height*.—Approximately 12.1 cm (measured from lowest flower/branching of raceme to top of inflorescence).

*Inflorescence width*.—Approximately 18.5 cm, racemes approximately 8.6 cm.

Individual flowers:

*Flower type*.—Single zygomorphic.

*Length* (*height*).—Approximately 4.7 cm.

*Width*.—Approximately 4.8 cm.

*Depth*.—Approximately 2.7 cm.

*Shape*.—Obovate.

*Fragrance*.—No fragrance.

*Persistent*.—Non-persistent.

*Petals*.—Arrangement: One petal on each side of the column. Length: Approximately 2.5 cm. Width: Approximately 2.7 cm. Quantity: 2. Shape: Deltoid. Apex: Rounded. Base: Cuneate. Margin: Entire. Texture: Upper (forward) surface: smooth, dull, moderately velvety. Texture: Lower (back) surface: smooth, dull, moderately velvety. Color: When opening, forward surface: White, near RHS N155B, center very light flushed Purple, near RHS 76D but lighter. When opening, back surface: White, near RHS N155B, center flushed violet, near RHS 84B. Fully Opened, forward surface: White, near RHS N155C, with a very small violet central spot; near RHS 84B. Fully Opened, back surface: White, near RHS N155C, center flushed violet, near RHS 84B to 84C. Fading, forward surface: Purple-violet, near RHS N80D, margin white, near RHS N155B. Fading, back surface: purple-violet, near RHS N80D, margin white, near RHS N155B. Color Venation Fully Opened, forward surface: No vein coloration. Fully Opened, back surface: No vein coloration.

*Labellum*.—Shape: Three-parted. Length: Approximately 1.8 cm. Width: Approximately 1.7 cm. Texture: Smooth, dull, slightly velvety. Tip: Cleft. Base: Cuneate. Color: When opening, forward surface: Central lobe white, near RHS N155D, lower half colored yellow, near RHS 12B. Lateral lobes white, near RHS 155C, margin on lower side yellow, near RHS 7A, base dotted red-purple, near RHS 59B. Callosities yellow, near RHS 13C, dotted red-purple, near RHS 59B. When opening, back surface: Central lobe white, near RHS N155C, lower half yellow, near RHS 7C, Lateral lobes white, near RHS 155C, margin on lower side yellow, near RHS 7A. Fully Opened, forward surface: Central lobe white, near RHS N155D, lower half colored yellow, near RHS 13A. Lateral lobes white, near RHS N155C, margin on lower side yellow, near RHS 13A, base dotted red-purple, near RHS 59B. Callosities yellow, near RHS 14A, dotted red-purple, near RHS 59B. Fully Opened, back surface: Central lobe white, near RHS N155C, lower half yellow, near RHS 13A to 13B, Lateral lobes white, near RHS 155C, margin on lower side yellow, near RHS 13A and 13B. Fading, forward surface: Not fading. Fading, back surface: Not fading. Color Venation Fully Opened, forward surface: No venation visible. Fully Opened, back surface: No venation visible. Margin: entire.

Sepals:

*Quantity*.—3.

*Appearance*.—Smooth, dull, moderately velvety.

*Length*.—Approximately 2.6 cm.

*Width*.—Approximately 1.9 cm.

*Shape*.—Ovate to elliptic.

*Apex*.—Obtuse.

*Base*.—Broad cuneate.

*Margin*.—Entire.

*Texture*.—Smooth, dull, moderately velvety.

*Color*.—Fully Opened, forward surface: White, near RHS N155D, very slightly flushed purple, near RHS 76C. Fully Opened, back surface: White, near RHS N155D, slightly flushed Purple, near RHS 76C with a purple central vein; near RHS 75A.

Pedicels:

*Length*.—Approximately 3.1 cm.

*Diameter*.—Approximately 0.3 cm.

*Angle*.—Approximately 85° to peduncle.

*Strength*.—Moderately strong.

*Texture*.—Smooth, moderately glossy.

*Color*.—Yellow-green, near RHS147C, distal part purple, RHS 75A and 75B.

REPRODUCTIVE ORGANS

*Stamens, style and stigma fused into column*.—Yes.

*Column length*.—Approximately 0.8 cm.

*Column diameter*.—Approximately 0.5 cm.

*Column color*.—White, near RHS N155C.

*Ovary*.—Position: Inferior. Diameter: Approximately 0.3 cm. Color: Green-white, near RHS 157D.

*Pollinia color*.—Yellow-orange, near RHS 21A.

OTHER CHARACTERISTICS

Disease resistance: Neither resistance nor susceptibility to the normal diseases found in *Phalaenopsis* has been observed.

Drought tolerance and cold tolerance: Normal for species.

Fruit/seed production: No fruits/seeds detected to date.

What is claimed:

1. A new and distinct cultivar of *Phalaenopsis* plant named 'SUPHAL1201' as herein illustrated and described.

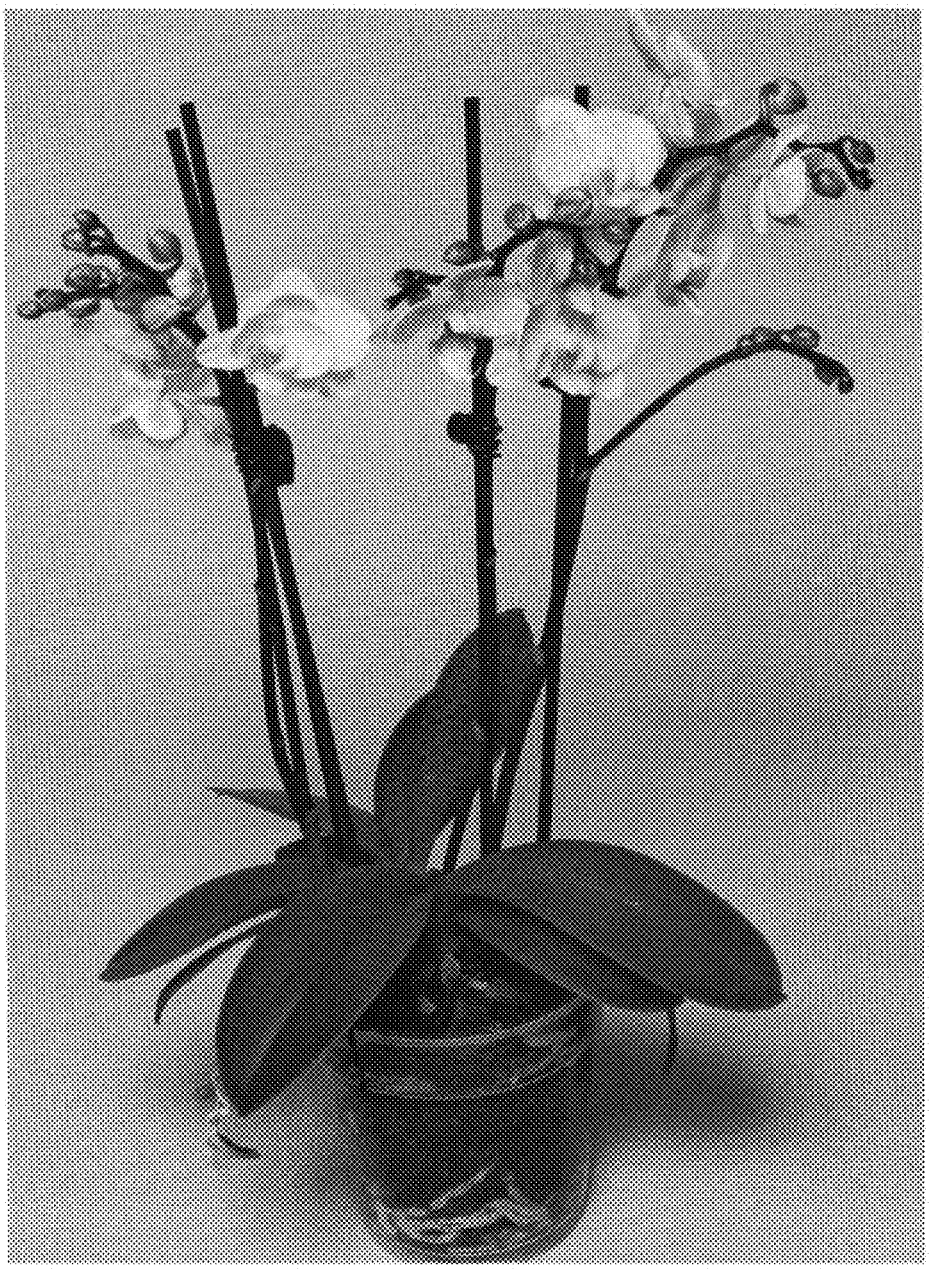

* * * * *